US010067564B2

(12) United States Patent
Smoot et al.

(10) Patent No.: US 10,067,564 B2
(45) Date of Patent: Sep. 4, 2018

(54) IDENTIFYING HAND GESTURES BASED ON MUSCLE MOVEMENT IN THE ARM

(71) Applicant: Disney Enterprises, Inc., Burbank, CA (US)

(72) Inventors: Lanny S. Smoot, Thousand Oaks, CA (US); Michael P. Goslin, Sherman Oaks, CA (US); Daniel James Reetz, Sunnyvale, CA (US); Joseph L. Olson, Los Angeles, CA (US)

(73) Assignee: Disney Enterprises, Inc., Burbank, CA (US)

( * ) Notice: Subject to any disclaimer, the term of this patent is extended or adjusted under 35 U.S.C. 154(b) by 388 days.

(21) Appl. No.: 14/823,685

(22) Filed: Aug. 11, 2015

(65) Prior Publication Data

US 2017/0045946 A1 Feb. 16, 2017

(51) Int. Cl.
*G06F 3/01* (2006.01)
*G06F 3/03* (2006.01)
(Continued)

(52) U.S. Cl.
CPC ............ *G06F 3/014* (2013.01); *A61B 5/6824* (2013.01); *G06F 1/163* (2013.01); *G06F 3/011* (2013.01);
(Continued)

(58) Field of Classification Search
CPC .. G06F 1/163; G06F 3/014; G06F 2203/0331; G06F 21/32; G06F 3/044; H01G 5/16; B42D 15/085; B42D 2033/46; B42D 25/355; A45C 11/00; A45C 13/008; A45C 2011/002; A44C 5/00; A44C 5/07;
(Continued)

(56) References Cited

U.S. PATENT DOCUMENTS 5,113,533 A * 5/1992 Takada .................. G08B 5/004
                                                                      2/1
6,104,379 A    8/2000 Petrich et al.
(Continued)

FOREIGN PATENT DOCUMENTS

WO       2009044967 A1     4/2009

OTHER PUBLICATIONS

Ma, Yinghong et al., Magnetic Hand Tracking for Human-Computer Interface, IEEE Transactions of Magnetics, vol. 47, Issue 5, 2010, IEEE, Piscataway, United States.
(Continued)

*Primary Examiner* — Sanjiv D Patel
(74) *Attorney, Agent, or Firm* — Patterson + Sheridan, LLP

(57) ABSTRACT

Embodiments described herein include an arm band that captures sensor data used to identify hand gestures. When worn on the arm, the arm band permits a computing device to identify different gestures made by the hand. In one embodiment, the band measures a change in position of the tendons that control the positions of the fingers on the hand which can then be correlated to a particular hand gesture. For example, the thickness of the user's arm increases in a direction perpendicular to the palm of the hand when the fingers are extended relative to the thickness of the arm when the fingers are curled into the palm of the hand. By detecting this change in thickness, the computing device can distinguish between different gestures.

14 Claims, 8 Drawing Sheets

(51) Int. Cl.
  *G06T 11/20* (2006.01)
  *G06T 7/00* (2017.01)
  *A61B 5/00* (2006.01)
  *G06F 1/16* (2006.01)
  *A44C 5/00* (2006.01)

(52) U.S. Cl.
  CPC ............... *G06F 3/017* (2013.01); *G06F 3/03* (2013.01); *G06T 7/0022* (2013.01); *G06T 11/206* (2013.01); *A44C 5/00* (2013.01)

(58) Field of Classification Search
  CPC .......... G01B 7/023; G01B 7/14; G01B 11/06; G01B 5/14; G01B 7/06; G01B 7/02; G01B 7/044; G01B 7/22; G01D 7/22; G01D 5/2417; G01D 3/036; G01D 5/24
  See application file for complete search history.

(56) References Cited

U.S. PATENT DOCUMENTS

| | | |
|---|---|---|
| 6,669,600 B2 | 12/2003 | Warner |
| 7,038,658 B2 | 5/2006 | Seki et al. |
| 8,246,462 B1 | 8/2012 | Tran et al. |
| 2005/0156587 A1* | 7/2005 | Yakymyshyn ........ G01R 15/207 324/117 R |
| 2012/0029399 A1 | 2/2012 | Sankai |
| 2012/0130202 A1 | 5/2012 | Jain |
| 2012/0157886 A1* | 6/2012 | Tenn .................. A61B 5/04888 600/595 |
| 2012/0319940 A1 | 12/2012 | Bress et al. |
| 2013/0293218 A1* | 11/2013 | Levesque ............... G01R 15/22 324/96 |
| 2014/0085077 A1 | 3/2014 | Luna et al. |
| 2014/0085177 A1* | 3/2014 | Lyons .................... G06F 3/014 345/156 |
| 2014/0094675 A1 | 4/2014 | Luna et al. |
| 2014/0206955 A1 | 7/2014 | Stivoric et al. |
| 2014/0214206 A1 | 7/2014 | Steinberg et al. |
| 2014/0240223 A1* | 8/2014 | Lake ..................... G08C 17/02 345/156 |
| 2014/0245783 A1 | 9/2014 | Proud et al. |
| 2014/0245784 A1 | 9/2014 | Proud et al. |
| 2014/0245785 A1 | 9/2014 | Proud et al. |
| 2014/0245786 A1 | 9/2014 | Proud et al. |
| 2014/0245788 A1 | 9/2014 | Proud et al. |
| 2014/0245789 A1 | 9/2014 | Proud et al. |
| 2014/0245791 A1 | 9/2014 | Proud et al. |
| 2014/0246499 A1 | 9/2014 | Proud et al. |
| 2014/0246502 A1 | 9/2014 | Proud et al. |
| 2014/0247151 A1 | 9/2014 | Proud et al. |
| 2014/0267123 A1 | 9/2014 | Ludwig |
| 2014/0354302 A1* | 12/2014 | Lu ..................... G01R 19/0084 324/658 |
| 2015/0101423 A1* | 4/2015 | Tuli ........................ G01P 13/00 73/865.4 |
| 2015/0186628 A1* | 7/2015 | Bush ...................... G06F 21/31 726/19 |
| 2016/0299570 A1* | 10/2016 | Davydov ................ G06F 1/163 |

OTHER PUBLICATIONS

Ma, Y. et al., Magnetic hand motion tracking system for human-machine interaction, Electronics Letters, Apr. 29, 2010, vol. 46, No. 9, The Institution of Engineering and Technology, Stevenage, United Kingdom.

Bainbridge, Rachel M., HCI Gesture Tracking Using Wearable Passive Tags, Submitted to the Department of Eletrical Engineering and Computer Science in partial fulfillment of the requirements for the degree of Master of Engineering in Electrical Engineering and Computer Science, Sep. 2010, pp. 1-80, MIT, Cambridge, United States.

* cited by examiner

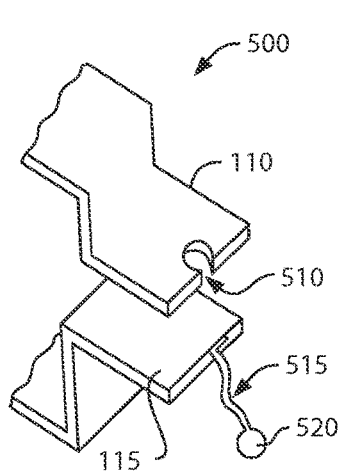
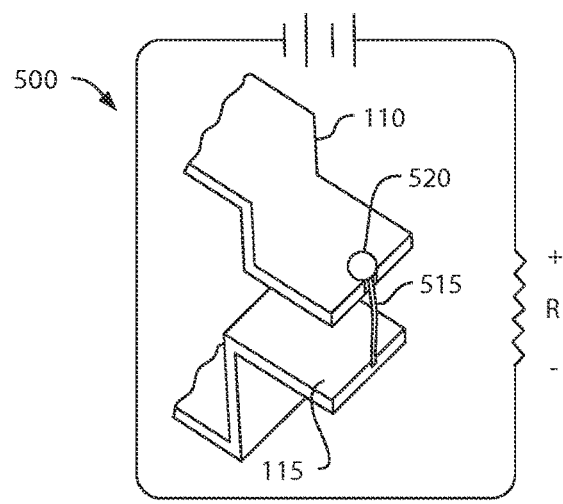
FIG. 5A
FIG. 5B
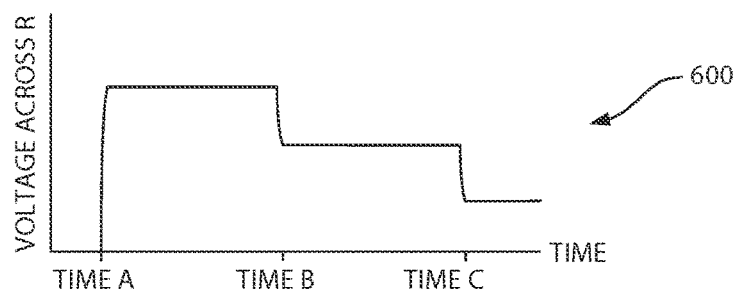
FIG. 6
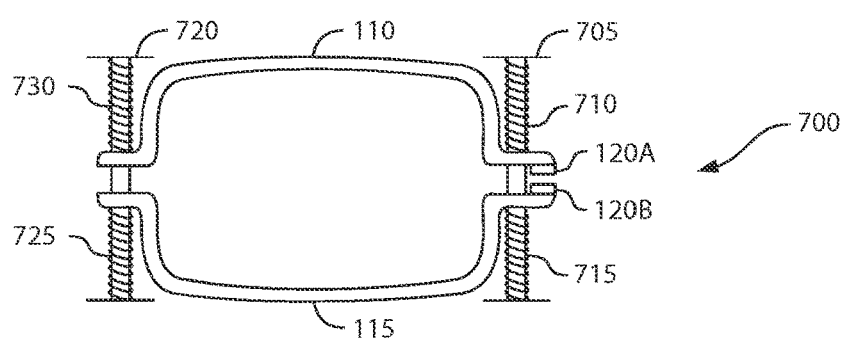
FIG. 7

US 10,067,564 B2

IDENTIFYING HAND GESTURES BASED ON MUSCLE MOVEMENT IN THE ARM

BACKGROUND

Field of the Invention

Embodiments presented in this disclosure generally relate to identifying hand gestures using signals generated by a band worn on an arm of a user.

Description of the Related Art

Detecting hand gestures made by a user can be used in a variety of applications such as gaming, interacting with a visual display, providing instructions to a computing device, and the like. Some gesture recognition systems detect hand gestures by capturing video images of the hand and then correlating these images to a particular gesture. However, these systems require expensive devices such as cameras that are typically mounted external to the user—i.e., are not carried by the user. Other gesture recognition systems may use sensors mounted on the hand such as rings worn on the fingers. However, these systems encumber the user and may limit the range of motion of the hand.

SUMMARY

One embodiment described herein is an arm band that includes a first portion, a second portion, a pivoting element, and a sensor. The pivoting element is coupled to respective first ends of the first and second portions and the pivoting element permits respective second ends of the first and second portions opposite of the first ends to separate relative to each other. The sensor is configured to, when the arm band is worn on the arm, generate an output signal indicative of a thickness of the arm in a direction substantially perpendicular to a palm of a hand.

Another embodiment described herein is a system that includes an arm band and a computing device. The arm band includes a first portion, a second portion, a pivoting element, and a sensor. The pivoting element is coupled to respective first ends of the first and second portions and permits respective second ends of the first and second portions opposite of the first ends to separate relative to each other. The sensor is configured to, when the arm band is worn on the arm, generate an output signal indicative of a thickness of the arm in a direction substantially perpendicular to a palm of a hand. Moreover, the computing device is configured to receive the output signal and determine a hand gesture causing the thickness of the arm to change.

Another embodiment described herein is an arm band that includes a rigid portion and a sensor array disposed on a surface of the rigid portion configured to face an arm. The sensor array includes a plurality of pressure sensors extending in at least two directions on the surface. Moreover, each pressure sensors is configured to generate an output signal indicative of pressure exerted on the pressure sensors by the arm.

BRIEF DESCRIPTION OF THE DRAWINGS

So that the manner in which the above recited aspects are attained and can be understood in detail, a more particular description of embodiments of the invention, briefly summarized above, may be had by reference to the appended drawings.

It is to be noted, however, that the appended drawings illustrate only typical embodiments of this invention and are therefore not to be considered limiting of its scope, for the invention may admit to other equally effective embodiments.

FIGS. 5A and 5B illustrate a clasping mechanism for an arm band, according to one embodiment described herein.

FIG. 6 is a chart for detecting hand gestures based on sensor output, according to one embodiment described herein.

FIG. 7 illustrates a band for detecting hand gestures, according to one embodiment described herein.

To facilitate understanding, identical reference numerals have been used, where possible, to designate identical elements that are common to the figures. It is contemplated that elements disclosed in one embodiment may be beneficially utilized on other embodiments without specific recitation.

DETAILED DESCRIPTION

Figure 1A:
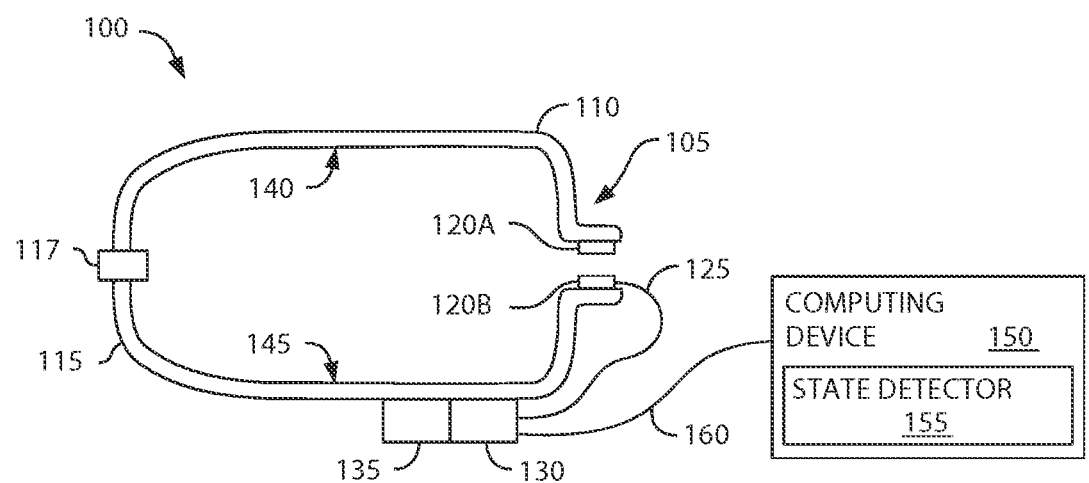
FIGS. 1A and 1B illustrate an arm band for detecting hand gestures, according to one embodiment described herein.

Embodiments described herein include an arm band that captures sensor data used to identify hand gestures. When worn on the arm, the arm band permits a computing device to identify different gestures made by the hand. In one embodiment, the band measures a change in position of the tendons and/or muscles that control the positions of the fingers on the hand which can then be correlated to a particular hand gesture. For example, the thickness of the user's arm increases when the fingers are extended relative to the thickness of the arm when the fingers are curled towards the palm of the hand. By detecting this change in thickness, the computing device can distinguish between different gestures.

In one embodiment, the arm band includes first and second portions that are attached to one another via a pivoting element (e.g., a hinge or flexible material) that permits the first and second portions to change positions relative to each other. The first and second portions may each have a flat surface configured to be positioned on opposite sides of a user's arm. In one embodiment, the flat surfaces may be disposed on opposing sides of the arm that are parallel with the palm of the hand. As the user makes different hand gestures, the tendons and muscles in the arm change the shape of the arm, thereby altering the thickness of the arm in a direction substantially perpendicular to the palm and the flat surfaces of the first and second portions. As the thickness changes, the pivoting element permits the first and second portions to move closer together or farther apart. For example, the pivoting element may include a spring (i.e., a clamping element) that causes the first and second portions to apply a clamping force on the arm which permits the relative positions of the first and second portions to change as the thickness of the arm changes. The band also includes a sensor (e.g., a magnetometer, voltage detector, or potentiometer) whose output signal changes as the distance between the first and second portions changes. By monitoring the output signal, a computing device can distinguish between different hand gestures without requiring external cameras or locating any sensors on the user's hand.

In another embodiment, the first and second portions of the band include apertures on both sides that slide along guide posts which permit the distance between the first and second portions to change. The guide posts may include springs (i.e., clamping elements) that apply a force that causes the first and second portions to clamp onto the arm of the user. As above, when the user makes different hand gestures, the distance between the first and second portions alters which changes an output signal of one or more sensors located on the band. By monitoring this change, a computing device can detect different hand gestures.

In another embodiment, an arm band includes an array of 2D pressure sensors for capturing a pressure image of the arm of the user. For example, the 2D array may include multiple pressure sensors arranged in rows and columns. Each of the pressure sensors may correspond to a pixel (e.g., a defined region) in the pressure image. The different measured pressures can be correlated to unique gray scale levels or different colors to generate the pressure image. Because different hand gestures may result in distinguishable pressure images, the computing device can evaluate a captured image to determine a particular hand gesture. For example, the user may have performed a calibration process and determined pressure images for a plurality of hand gestures. By comparing the current pressure image to the images captured during the calibration process, the arm band can identify a particular hand gesture. Evaluating a pressure image captured using a 2D array of sensors may provide additional granularity for distinguishing between two gestures that may appear to be similar if, for example, the band only measured a change in the arm's thickness.

Moreover, the length of the 2D array in the direction at which the arm extends may be set so that the band can continue to identify gestures even if the position of the band on the arm changes. For example, after calibrating the band using a set of hand gestures, the user may take the band off. When the user puts the band back on, the band may be oriented differently (i.e., located at a different position or rotated) on the arm. Instead of requiring the user to repeat the calibration process, the computing device may request the user make a single hand gesture which can be used to correlate the current pressure image captured by the band to a pressure image captured during calibration. By identifying an overlap in the pressure images, the computing device determines a transformation function that can be used to correlate the current pressure images captured when the band is at the new orientation on the arm to the images captured during calibration. Thus, even if the band is moved to a different location, the computing device can still identify the hand gestures used in the calibration process.

Figure 1B:
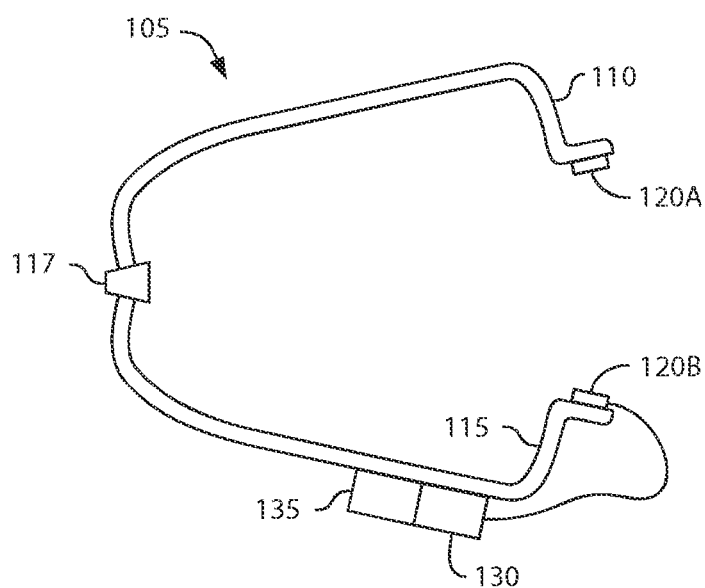

FIGS. 1A and 1B illustrate an arm band 105 for detecting hand gestures, according to one embodiment described herein. As shown, system 100 includes arm band 105 and a computing device 150. The arm band 105 includes a first portion 110 and a second portion 115 that are coupled using a pivoting element 117 which provides a pivot point for changing the spatial relationship between the first and second portions 110, 115. In one embodiment, the pivoting element 117 is a hinge with a rotational axis that permits an end of the first portion 110 that is opposite the pivoting element 117 to move away from a corresponding end of the second portion 115 to form an opening to receive an arm of a user. Alternatively, the pivot element 117 may be a flexible material—e.g., rubber or other elastic material—that couples the first portion 110 to the second portion 115 but nonetheless permits the two portions to move relative to each other.

In one embodiment, the pivot element 117 asserts a clamping force on the first and second portions 110, 115 that urges these portions towards each other—i.e., force the distal ends of the first and second portions 110, 115 (which are opposite the ends connected to the pivoting element 117) to contact. For example, the pivoting element 117 may include a clamping element such as a spring that applies the clamping force, or the element 117 may include flexible material that applies the clamping force which resists a force attempting to open the band 105 by separating the first portion 110 from the second portion 115.

The first and second portions 110, 115 include respective flat surfaces 140, 145 located between the respective ends of the portions 110, 115. Although not required, the flat surfaces 140, 145 each provide an even surface for contacting the tendons in the arm of the user. A flat surface may be preferred over a curved surface since a flat surface more accurately mimics the shape of the arm near the wrist on the opposing sides of the arm parallel with the palm of the hand. As such, the flat surfaces 140, 145 may be affected more by movement of the tendons in the wrist relative to a curved surface. When the arranged on the arm such that the flat surfaces 140, 145 are parallel with the palm of the hand, the pivoting element 117 faces a side of the arm perpendicular to the palm of the hand. As the tendons and muscles change the shape of the arm, they alter the thickness of the arm in a direction substantially perpendicular to the flat surfaces 140, 145. Stated differently, the movement of the tendons and muscles alters the thickness of the arm in a direction substantially perpendicular to the palm of the hand. As used herein, "substantially perpendicular" means that when worn on the arm, the flat surfaces 140, 145 may not be perfectly parallel, and thus, the thickness of the arm measured by the first and second portions 110, 115 may not be exactly perpendicular to the flat surfaces 140, 145 or to the palm of the hand. For example, the thickness of the arm may change in a direction that is 10-15 degrees removed from being perpendicular from one or both of the flat surfaces 140, 145. Moreover, as the tendons cause the thickness of the arm to increase, the resulting pivoting motion causes the flat surfaces 140, 145 to become farther away from being in parallel to each other.

A sensor 120 is disposed on ends of the first and second portions 110, 115 that are opposite the pivoting element 117. In one embodiment, the sensor 120 generates an output signal that changes based on the separation distance between the first and second portions 110, 115. To do so, the sensor 120 includes a first sensor portion 120A and a second sensor portion 120B. If the sensor 120 is a magnetometer, the first sensor portion 120A may be a permanent magnet while the second sensor portion 120A may be a hall-effect sensing device. As the magnet moves away from the sensing device—i.e., the separation distance between the first and second portions 110, 115 increases—the output signal of the sensor 120 decreases. Conversely, as the first and second sensing portions 120A, 120B come closer together, the output signal increases. In other embodiments, the sensor 120 may include a linear or rotational potentiometer or an optical system where a transmitter emits radiation detected by a detector. Generally, the sensor 120 may be any detection system that generates an output signal (digital or analog) that varies according to the separation distance of the first and second portions 110, 115.

The second sensing portion 120B is coupled to a transmitter 130 and a battery 135 via a cable 125. The transmitter 130 receives the output signal generated by the sensor 130 which is then forwarded to the computing device 150. The battery 135 provides power to the sensor 120 in order to generate the output signal. Although the cable 125 is shown here to provide a path for power to reach the sensor 120 as well as a path for the output signal to reach the transmitter 130, in other embodiments, the band 105 may use different cablings or wires to transmit power and the output signal. Furthermore, instead of mounting the battery 135 onto the band 105, an external component (e.g., computing device 150) may provide power to the sensor 120.

As shown, the computing device 150 includes a state detector 155 but may also include one or more processors and memory. For example, the computing device 150 may be a server, desktop computer, laptop, smartphone, tablet, and the like. In other embodiments, the computing device 150 may be a special purpose computing device rather than a general purpose computing device. The computing device 150 may include an ASIC that contains logic for processing the signals received from the transmitter 130. For example, the computing device 150 may include special hardware for processing the output signals and outputting an indicator when the signal crosses a predefined threshold (e.g., turns on an LED or outputs a beep). Although the computing device 150 is shown as being external to the arm band 105, in other embodiments, the computing device 150 can have a small enough form factor to be disposed on the band 105.

The state detector 155 processes the signals received from the transmitter 130 via connection 160. The state detector 155 may be implemented as software, hardware, firmware, or some combination thereof in the computing device 150. Moreover, the connection 160 may be a wired or wireless communication link.

As described below, the state detector 155 monitors the signal outputted from the sensor 120 to identify gestures may the hand of the user. That is, as the tendons of the arm cause the surface of the arm to bulge and change the output signal of the sensor 120, the state detector 155 correlates the change in the output signal to a particular hand gesture. To do so, the state detector 155 may compare the output signal to one or more thresholds or monitor the percentage of change in the output signal to distinguish between different hand gestures. Regardless of the technique used, the system 100 is able to identify hand gestures without relying on any sensors on the hand or an external camera system used to capture visual images of the hand.

In one embodiment, the first and second portions 110, 115 are made of a rigid structure—e.g., plastic or metal. Furthermore, a flexible or pliable substrate may be disposed on the flat surfaces 140, 145 such as rubber, foam, and the like. The flexible substrate may be between the rigid (hard) material of the first and second portions 110, 115 and the skin of the use to improve comfort. The stiffness and thickness of the substrate may be controlled such that movement in the tendons is not absorbed by the substrate thereby preventing the first and second portions 110, 115 from separating in response to different hand gestures.

While FIG. 1A illustrates the band 105 in a closed state, FIG. 1B illustrates the band 105 in an open state. For example, the closed state may be a result of the clamping force caused by the pivoting element 117 which forces the ends of the first and second portions 110, 115 containing the first and second sensor portions 120A, 120B to move closer together (or touch). In another embodiment, instead of using a clamping force, the band 105 may include a latching mechanism proximate to the sensor 120 that permits the user to keep the band 105 securely on the arm. For example, an elastic band may stretch between the ends near the sensor 120 to keep the first and second portions 110, 115 in the closed state. As the tendons in the arm bulge out, the elastic band permits the first and second portions 110, 115 to separate as reflected in the output signal of the sensor 120.

The open state shown in FIG. 1B may be useful when a user first positions the band 105 on her arm. To achieve the open state, the user may exert a force that overcomes the clamping force generated by the pivoting element 117. Alternatively, the user may unlock the latching mechanism such that the first and second portions 110, 115 can pivot freely. Once the arm is placed between the first and second portions 110, 115, the band 105 is put into the closed state.

Figure 2:
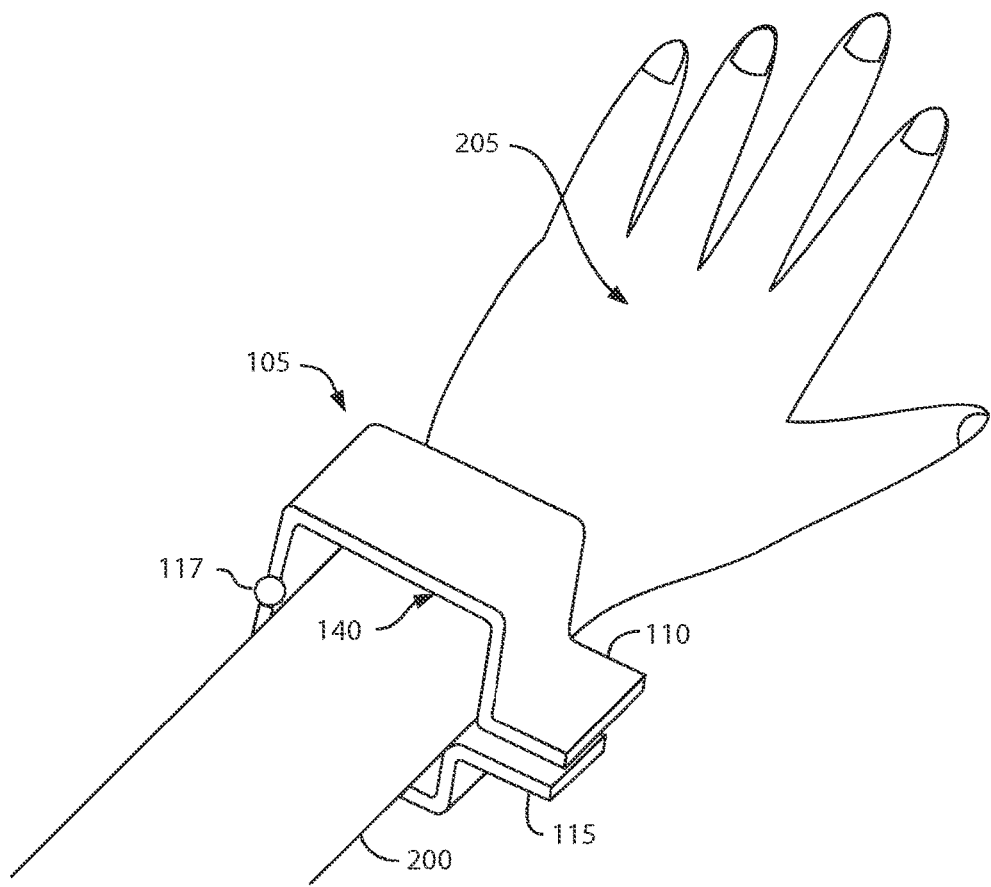
FIG. 2 illustrates an arm band, according to one embodiment described herein.

FIG. 2 illustrates the band 105 located on an arm 200 of a user, according to one embodiment described herein. In this example, the flat surface 140 on the first portion 110 is on the same side of the arm as the back of the hand 205. Of course, the band 105 could be rotated 180 degrees so that the flat surface 140 is aligned with the palm of the hand and still achieve the same function discussed herein. Although the band 105 may be located at any location on the arm between the hand and elbow, in one embodiment, the shape of the band 105 defined by the first and second portions 110, 115 may be designed to mimic the shape of the arm near the wrist of the user.

Figure 3A:
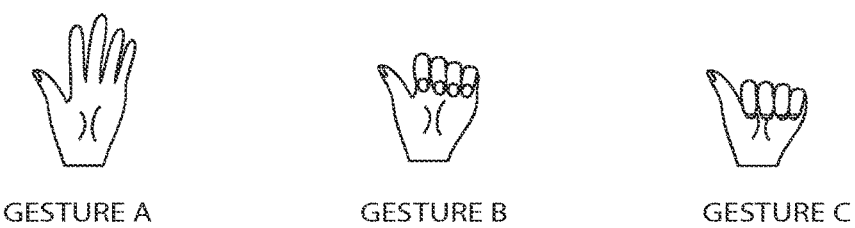
FIG. 3A illustrates different hand gestures detectable using the arm band, according to one embodiment described herein.

FIG. 3A illustrates different hand gestures detectable using the band, according to one embodiment described herein. Gesture A illustrates a hand where the fingers are extended such that the fingers and palm of the hand lie substantially on the same plane. When making this gesture, the tendons in the arm tend to protrude outward (in a direction perpendicular to the palm of the hand) thereby increasing the thickness of the arm, especially near the wrist. Gesture B illustrates a hand where the fingers are curled such that at least a portion of the fingers extend in a direction perpendicular to the palm of the hand. In this gesture, the fingers do not touch the palm of the hand. When making Gesture B, the tendons in the arm typically protrude less, and thus the arm has a smaller thickness, then when making Gesture A.

Gesture C illustrates a hand where the fingers are curled such that the tips of the fingers contact the palm of the hand. When making this gesture, the tendons in the arm typically protrude less than when making both Gestures A and B. As such, Gesture C may result in the arm having the smallest thickness compared to the thickness of the arm when making Gestures A and B. Moreover, clinching the first, rather than simply touching the tips of the fingers to the palm as shown in Gesture C may cause the thickness of the arm to again increase. For example, the thickness of the arm when making a clinched first may be the same or greater as when making Gesture A.

Figure 3B:
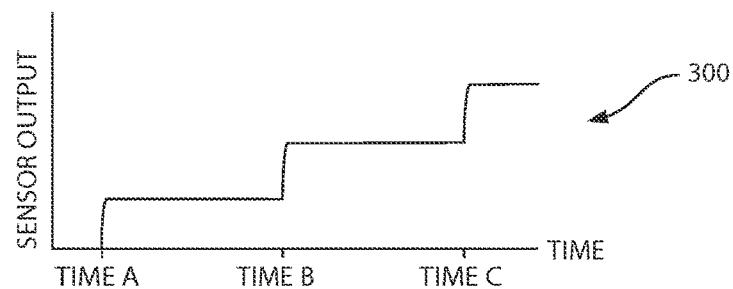
FIG. 3B is a chart for detecting hand gestures based on sensor output, according to one embodiment described herein.

FIG. 3B is a chart 300 for detecting hand gestures based on sensor output, according to one embodiment described herein. The x-axis illustrates the output of the sensor—e.g., sensor 120 in FIG. 1A. The output signal may be a voltage, current, pressure value, resistance value, etc. depending on the type of sensor disposed on the band. At Times A, B, and C, the user makes different hand gestures thereby changing the thickness of the arm and the sensor output. In this example, at Time A, the user makes Gesture A, at Time B, the user makes Gesture B, at Time C, the user makes Gesture C.

When using a magnetometer as the sensor, as the thickness of the arm decreases and the separate distance between the first and second portions 110, 115 shown in FIG. 1A decreases, the magnetometer output increases. Because the thickness of the arm is the greatest when making Gesture A at Time A, the output of the magnetometer is the smallest when making this gesture (assume that the band was in an open state before Time A). At Time B, the user makes Gesture B thereby decreasing the thickness of the arm and increasing the sensor output. At Time C, the user makes Gesture C which further decreases the thickness of the arm and increases the sensor output.

The state detector receives the sensor output and identifies the corresponding gesture. For example, the state detector may compare the current sensor output to one or more thresholds. Depending on which threshold the sensor output value is currently between, determines the gesture being made. Alternatively, the state detector may monitor the changes in the sensor output to identify the gesture. For example, the state detector may instruct the user to make a baseline gesture (e.g., Gesture A). As the user makes different gestures, the state detector monitors the change in the output to determine when the user is now making a different gesture—e.g., a 10% change from baseline indicates Gesture B, while a 20% change from baseline indicates Gesture C. Using a baseline gesture may be used to compensate for the different anatomy between different users. That is, the thickness of one user's arm when making Gesture A may be much different than the thickness of another user's arm when making the same gesture. By establishing a baseline for each individual user, the same band can identify gestures for different users with different arm thicknesses.

In one embodiment, the state detector performs a calibration process to correlate a sensor output to different gestures. The state detector may, using an output device such as a video monitor or speaker, ask the user to make different gestures (e.g., Gestures A-C). As the user makes the gestures, the state detector determines the sensor output corresponding to that gesture. So long as the sensor output is different for the different gestures, when the calibration process is complete, then the state detector can identify a spontaneous gesture made by the user. The calibration process may be repeated for each user or repeated each time the user puts on the band. Alternatively, calibrating the band once for one user may be sufficient even if the user takes off the band and then puts the band back on.

Furthermore, performing the calibration process or requesting the user make a baseline gesture may not be necessary. For example, the output signals generated by a user making Gesture A and Gesture C may be different enough that the state detector can identify the gesture as the user switches from one gesture to the other. For example, if the user makes Gesture A when putting on the band but then switches to Gesture C, the state detector can identify the large increase in the sensor output and determine that the user is making Gesture C. Even if different users have varying arm thicknesses, by measuring the change in the sensor output, the state detector can identify multiple gestures even if the absolute values of the sensor output for different users when making the gestures are very different.

Figure 4A:
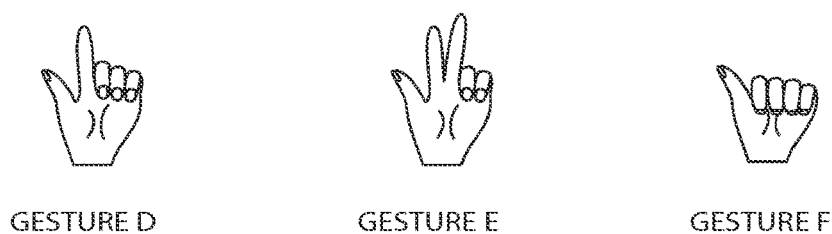
FIG. 4A illustrates different hand gestures detectable using the arm band, according to one embodiment described herein.

FIG. 4A illustrates different hand gestures detectable using the band, according to one embodiment described herein. Gesture D illustrates a hand where the pointer finger is extended while the remaining fingers are curled to touch the palm of the hand. In this gesture, the pointer finger and palm of the hand lie substantially on the same plane. When making Gesture D, the tendons in the arm tend to protrude outward in a direction perpendicular to the palm of the hand thereby increasing the thickness of the arm in this direction, especially near the wrist. Gesture E illustrates a hand where the pointer and middle fingers are extended while the remaining fingers are curled to touch the palm of the hand. The pointer and middle fingers extend in a direction perpendicular to the palm of the hand. When making Gesture E, the tendons in the arm typically protrude more than Gesture D, and thus the arm has a greater thickness in the direction perpendicular to the palm of the hand.

Gesture F illustrates a hand where the fingers are curled such that the tips of the fingers contact the palm of the hand—i.e., the same as Gesture C shown in FIG. 3B. When making this gesture, the tendons in the arm typically protrude less than when making both Gestures D and E. As such, Gesture F may result in the arm having the smallest thickness compared to the thickness of the arm when making Gestures D and E. Moreover, clinching the first, rather than simply touching the tips of the fingers to the palm as shown in Gesture F may cause the thickness of the arm to again increase. For example, the thickness of the arm when making a clinched first may be the same or greater as when making Gesture E.

Figure 4B:
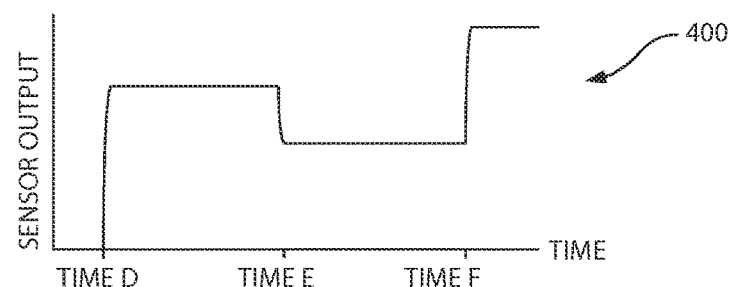
FIG. 4B is a chart for detecting hand gestures based on sensor output, according to one embodiment described herein.

FIG. 4B is a chart 400 for detecting hand gestures based on sensor output, according to one embodiment described herein. The x-axis illustrates the output of the sensor—e.g., sensor 120 in FIG. 1A. The output signal may be a voltage, current, pressure value, resistance value, etc. depending on the type of sensor disposed on the band. At Times D, E, and F, the user makes different hand gestures thereby changing the thickness of the arm and the sensor output. In this example, at Time D, the user makes Gesture D, at Time E, the user makes Gesture E, and at Time F, the user makes Gesture F.

If a magnetometer is the sensor, as the thickness of the arm decreases and the separation distance between the first and second portions 110, 115 shown in FIG. 1A decreases, the output increases. At Time D when making Gesture D, the sensor output generates a middle output level. When making Gesture E at Time E, the thickness of the arm increases relative to making Gesture D. Because this increase in thickness separates the first and second portions 110, 115, the signal generated by the sensor falls to a low output level. At Time F, the user makes Gesture F which decreases the thickness of the arm and increases the sensor output to a high output level.

The state detector receives the sensor output and identifies the corresponding gesture. For example, the state detector may compare the current sensor output to one or more thresholds. Determining which threshold the sensor output value is currently between, determines the gesture being made. Alternatively, the state detector may monitor the changes in the sensor output to identify the gesture. For example, the state detector may instruct the user to make a baseline gesture as discussed above. Moreover, the state detector may perform a calibration process in order to distinguish between Gestures D, E, and F by measuring a calibration signal indicative of the thickness of the arm of the user for these different gestures. The state detector can then compare the current output signal to the calibration signals and determine which one is closest, thereby identifying the hand gesture currently being made by the user.

FIGS. 5A and 5B illustrate a clasping mechanism for an arm band 500, according to one embodiment described herein. Although not shown, the band 500 may include a pivoting element disposed on an opposite side as the side shown here. In one embodiment, the pivoting element does not include a clamping mechanism (e.g., a spring) that generates a clamping force that moves portion 110 closer to portion 115. Instead, the clasping mechanism shown in FIG. 5A enables the user to clasp the first portion 110 to the second portion 115 in a closed state.

The clasping mechanism includes a receiving element 510, elastic band 515, and connector ball 520. The receiving element 510 includes a surface that defines an aperture with a circumference that may be equal to, or smaller than the connector ball 520. For example, the surface in the receiving element 510 may be sloped such that the connector ball 520 rests on the surface. The length of the elastic band 515 may be chosen so that the band 515 is stretched to create tension that pulls the first portion 110 toward the second portion 115 around a user's arm when the connector ball 520 is placed in the receiving element 510. In this manner, the tension in the elastic band 515 generates a clasping force that keeps the band 500 on the arm of a user.

FIG. 5B illustrates the arm band 500 when the connector ball 520 is placed in the receiving element 510 which may stretch the elastic band 515. In addition to providing the clasping force that keeps the band 500 in the closed state, the elastic band 515 may be conductive. Using a battery on the band 500, the elastic band 515 and ball 520 may be used to close an electric circuit. For example, the first and second portions 110, 115, elastic band 515 and connector ball 520 may be conductive such that the voltage applied by the battery generates a current that flows through the band 500 (which may be very small and unnoticeable to the user).

In one embodiment, the elastic band 515 is a variable resistor (R) whose resistance varies with its length. For example, as the band 515 is stretched and its length increases, its resistance may increase. Alternatively, as the band 515 shrinks, its electrical resistance may decrease. In one embodiment, changing the thickness of the arm changes the length of the elastic band 515, and thus, changes its resistance. Put differently, the resistance of the band 515 changes in direct correlation with the thickness of the arm. To measure that change in resistance, the band 500 may include a current, voltage, or resistance sensor coupled to the circuit shown in FIG. 5B. The output of the sensor changes as the resistance of the elastic band 515 increases or decreases. As the thickness of the arm changes (i.e., the user makes different hand gestures), the state detector evaluates the output signal generated by the sensor and determines the current hand gesture being made by the user.

FIG. 6 is a chart 600 for detecting hand gestures based on sensor output, according to one embodiment described herein. In one embodiment, the chart 600 illustrates the output of a sensor connected to the electric circuit shown in FIG. 5B—e.g., a current, voltage, or resistance sensor. For example, the sensor may measure a voltage across the elastic band 515 or the current running through the band 515. In this example, chart 600 illustrates the voltage across the band 515. Specifically, the chart 600 illustrates the voltage across the band when the user makes Gestures A, B, and C, shown in FIG. 3B. Time A illustrates the voltage across the elastic band 515 when the user makes Gesture A, Time B illustrates the voltage across the elastic band 515 when the user makes Gesture B, and Time C illustrates the voltage across the band 515 when the user make Gesture C. Because the thickness of the arm (in a direction perpendicular to the user palm) is the greatest when making Gesture A, at Time A the elastic band 515 is stretched the most (i.e., the tendons in the arm force the first portion 110 away from the second portion 115 which stretches the elastic band 515) which increases the resistance of the band 515 and the voltage drop across the band 515. However, at Time B when making Gesture B, the thickness of the arm is reduced which decreases the resistance of the band 515 and the voltage drop across the band 515. At Time C, the resistance of the band 515 and the voltage decrease further as the user makes Gesture C.

As discussed above, the state detector monitors the output of the sensor (voltage in this example) and correlates the output to a particular gesture—e.g., Gesture A, B, or C. Moreover, the state detector may use thresholds or monitor the change in the output signal to determine when the user makes different gestures. The state detector may use a baseline gesture or a calibration process to detect gestures for different users whose arms may have different thicknesses.

FIG. 7 illustrates an arm band 700 for detecting hand gestures, according to one embodiment described herein. Like the band 100 shown in FIG. 1, arm band 700 includes the first portion 110, second portion 115, and sensor 120. However, instead of using a pivoting element to move the band 700 into open and closed states, arm band 700 includes guide posts 705, 720 that provide guides for sliding and separating the first and second portions 110, 115. To do so, the first and second portions 110, 115 slide on the posts 705, 720 in a lateral direction—i.e., up and down relative to FIG. 7. Although not shown, the first and second portions 110, 115 may include apertures through which the posts are inserted. Moreover, the posts 705, 720 include stops at their respective ends to limit separation distance between the portions 110, 115 and prevent the first and second portions 110, 115 from coming off the posts 705, 720. When a user desires to insert her arm between the first and second portions 110, 115, she uses the posts 705, 720 to slide the first and second portions 110, 115 apart to provide enough room so that her hand can be inserted between the first and second portions 110, 115 (i.e., an open state). Once the band 700 is position in the desired location on her arm (e.g., the wrist), the user may use the posts 705, 720 to slide the first and second portions 110, 115 towards one another until they contact the arm of the user.

The arm band 700 includes upper and lower springs 710, 715, 725, 730 which wrap around the posts 705, 720. In this example, the upper springs 710 and 730 are disposed between the first portion 110 and respective upper ends of the posts 705, 720. As the user moves the first portion 110 towards these ends (for example, to open the band 700), this movement compresses the upper springs 710, 730. The lower springs 715, 725 are disposed between the second portion 115 and respective lower ends of the posts 705, 720. When the user moves the second portion 115 towards these lower ends, the lower springs 715, 725 are compressed. When the first and second portions 110, 115 are released, the springs 710, 715, 725, 730 generate a clamping force that compresses the first and second portions 110, 115 on the arm of the user of two different sides. This clamping force may enable the output of the sensor 120 to better represent the thickness of the arm relative to an arm band that does not generate a clamping force to maintain the band in a closed state.

Figure 8:
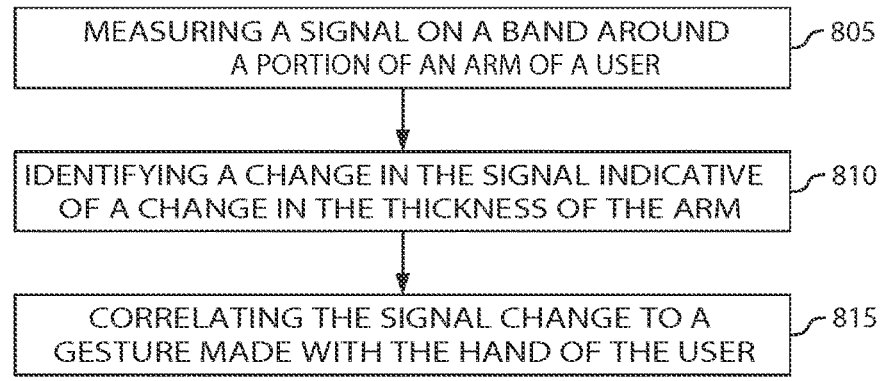
FIG. 8 is a flow chart illustrating a method for detecting hand gestures using an arm band, according to one embodiment described herein.

FIG. 8 is a flow chart illustrating a method 800 for detecting hand gestures using an arm band, according to one embodiment described herein. At block 805, the state detector measures a signal outputted by the arm band when it is disposed around an arm of a user. As described above, the arm band may include first and second portions that separate as the thickness of the arm (e.g., the wrist) changes in a direction perpendicular to the palm of the hand. The arm band includes a sensor that generates the output signal which varies as the separation distance of the first and second portions changes.

At block 810, the state detector identifies a change in the output signal indicative of a change in the thickness of the arm. For example, the state detector may be software or hardware disposed on a computing device separate from the arm band that receives updates from the sensor disposed on the band. By evaluating these updates, the state detector can identify changes in the sensor output. In other embodiments, the state detector may be logic located on the band itself.

At block 815, the state detector correlates the output signal to a hand gesture made by the user. In one embodiment, the state detector uses one or more thresholds to determine when the user has changed hand gestures. Using the gestures and chart 300 shown in FIGS. 3A and 3B as an example, the state detector may have two thresholds that are between the output signal levels that correspond to Gestures A, B, and C. If the output signal is less than the first threshold, the state detector knows the user is making Gesture A. If the output signal is greater than the first threshold but less than the second threshold, the state detector determines the user is making Gesture B. If the output signal is greater than the third threshold, the state detector determines the user is making Gesture C.

Alternatively, the state detector may monitor the changes in the output signal to identify the gesture. For example, the state detector may instruct the user to make a baseline gesture (e.g., Gesture A). As the user makes different gestures, the state detector monitors the change in the output to determine when the user makes a different gesture—e.g., a 10% change from baseline correlates to Gesture B, while a 20% change from baseline correlates to Gesture C. A baseline gesture may be used to compensate for the different anatomy between different users. By establishing a baseline for each individual user, the same arm band can identify gestures for different users with different arm thicknesses. Moreover, in other embodiments, the state detector may perform a calibration process to set the thresholds or determine the changes in the sensor output that are indicative of different gestures.

Identifying Gestures Using a 2D Array of Sensors

Figure 9:
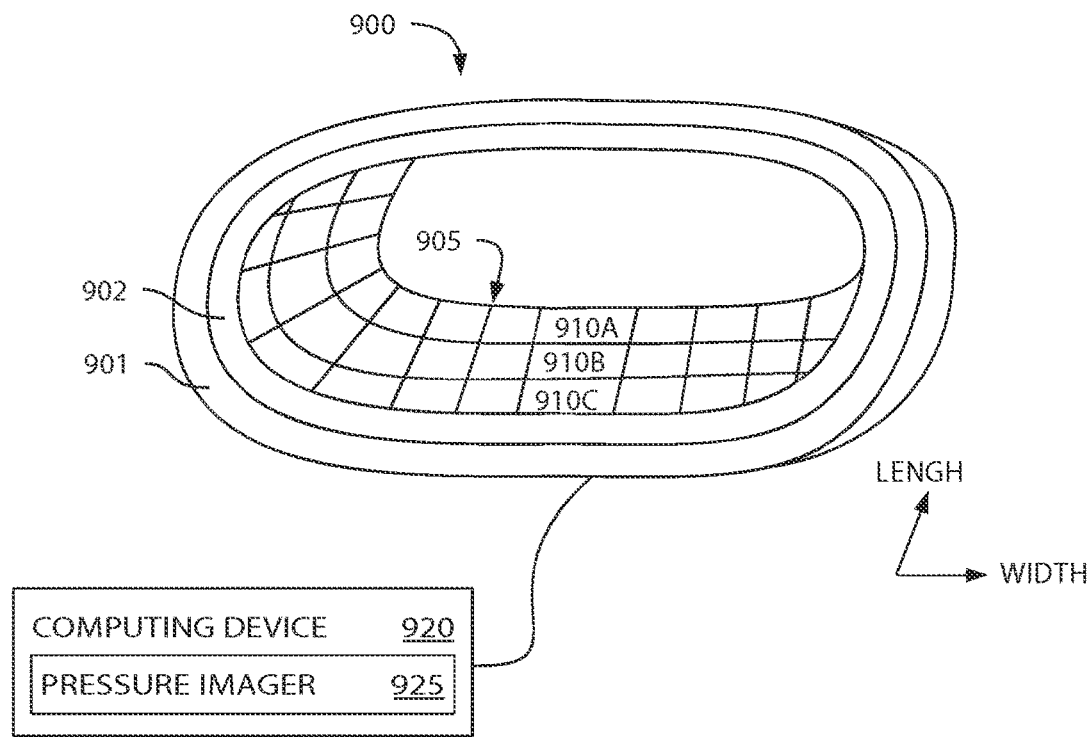
FIG. 9 illustrates an arm band containing a 2D array of pressure sensors, according to one embodiment described herein.

FIG. 9 illustrates an arm band 900 containing a 2D array of pressure sensors 905, according to one embodiment described herein. As shown, the arm band 900 includes an outer portion 901, an inner portion 902, and the sensor array 905. In one embodiment, the outer portion 901 includes a material (e.g., plastic or metal) that is rigid or inflexible relative to the inner portion 902. In contrast, the inner portion 902 may include a material that is flexible or pliable such as rubber or foam. When the user asserts her arm into the annular aperture formed by the outer and inner portions 901, 902, the rigid outer portion 901 provides a backstop allowing the tendons and muscles in the arm to compress the pliable material in the inner portion 902. Moreover, the shape of the inner and outer portions 902, 901 may match the general cross sectional shape of a human arm. When putting on the band 900, the user may slide the band up the arm until the arm fills the aperture created by the inner portion 902. For example, the user may position the band 900 on her arm until the arm contacts two opposite sides of the arm band 900.

The sensor array 905 is disposed on the inner portion 902. In one embodiment, the sensor array 905 covers the entire surface of the inner portion 902 that faces the arm of the user, though this is not a requirement. The sensor array 905 includes a plurality of individual pressure sensors 910. Although the sensor array 905 includes three pressure sensors 910 in the length direction (i.e., the same direction at which the arm extends) this is for illustration purposes only. In other embodiments, the array 905 may include hundreds of individual sensors forming a column extending in the length direction and thousands of sensors extending in the width direction to form individual rows. In one embodiment, the length of the band 900 may between half an inch to three inches. The circumference of the band 900 may match the average circumference of a human arm. Furthermore, the present disclosure is not limited to using pressure sensors to form the sensor array 905. In another embodiment, ultrasonic transducers may be used to form the array 905 where each transducer generates a small acoustic pulse and immediately measures the returned sound pressure in at its location. If the sound is reflected well, the arm band 900 may determine the skin is taut because it is disposed over a tensed tendon. But if the reflected sound is damped, the skin is flaccid and the underlying tendon is not tense. Based on the tendon tenseness determined at each transducer location, the arm band 900 can generate an image which can be processed as described below.

Each sensor 910 generates a respective output signal. For example, sensors 910A, 910B, and 910C generate respective output signals that are transmitted to the computing device 920 which can be located on, or external to, the arm band 900. The computing device 920 includes a pressure imager 925 that uses the output signals provided by the pressure sensor 910 to generate a digital pressure image. In one embodiment, each pressure sensor 910 corresponds to a pixel in the pressure image (i.e., a defined sub-region on the image). As the tendons in the arm press against the sensors 910, the sensors 910 generate different pressure values. The pressure imager 925 translates these pressure values into respective colors (or shades of a color). The imager 925 may use the colors corresponding to each pressure sensor 910 as pixels to generate the pressure image. In this example, the pressure image may have as many pixels as the number of pressure sensors 910 in the array 905. Alternatively, the pressure imager 925 may use the pressure values (and corresponding gray-scale or color values) to derive gray-scale or colors for other pixels in the image. In that scenario, the pressure image may contain more image pixels than the number of sensors 910. Using video processing techniques, the pressure images 925 can analyze the image to distinguish between hand gestures made by the user.

Although the arm band 900 is shown with outer and inner portions 901, 902 that form complete rings, the band 900 is not limited to such. For example, the sensor array 905 may be formed on the band 100 shown in FIG. 1A where the first and second portions 110, 115 may each include a 2D array of sensor (or only one of the portions 110, 115 include a 2D sensor array). In this example, the arm band may use the pivoting element 117 to open the band and permit the user to insert the band around her arm. A clamping element or latching mechanism can be used to exert a force that presses the sensors in the array onto the arm, thereby permitting the pressure imager 925 to generate the pressure images.

Figure 10:
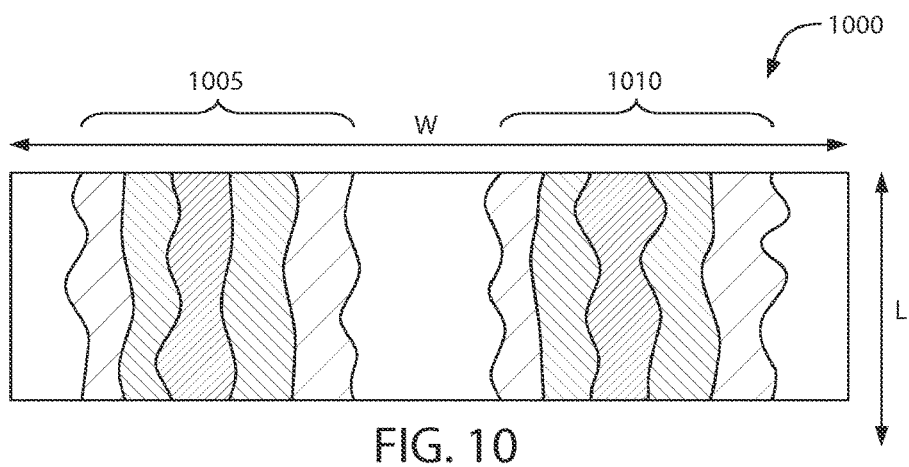
FIG. 10 illustrates a pressure image derived from the 2D array of sensors, according to one embodiment described herein.

FIG. 10 illustrates a pressure image 1000 derived from the 2D array of sensors, according to one embodiment described herein. To generate the image 1000, the pressure imager may translate the pressure values outputted by the individual pressure sensors in the array into respective gray-scale or color values (represented by the different densities of hatchings). As the tendons and muscles in the arm cause the outer surface of the arm to bulge, these movements cause the pressure values measured by the sensors on the band to change. The image 1000 represents the pressure the user's arm places on the band at a particular period of time.

The pressure image 1000 includes a first portion 1005 and a second portion 1010 that correspond to different pressure sensors in the sensor array, and thus, the user's arm. Because making different gestures with the hand causes the tendons and muscles located on the sides of the arm that are parallel to the palm of the hand to move the most, the pressure sensors contacting these sides of the arm measure the highest change in pressure values. For example, the first portion 1005 of image 1000 may correspond to the side of the arm that is on the same plane as the palm of the hand while second portion 1010 may correspond to the side of the arm that is on the same plane as the back of the hand. The portions of the image 1000 between the first and second portions 1005, 1010 may correspond to the more boney parts of the wrist where the tendons making the hand gestures do not cause the outer surface of the arm to bulge. Thus, these portions of the image 1000 are assigned colors corresponding to smaller measured pressure values.

The width and the length of the pressure image 1000 may correspond to the dimensions of the sensor array 905 shown in FIG. 9. For example, the number of pixels (and their density) may vary according to the number of pressure sensors 910 in the array 905. For instance, as the length of the array 905 increases (e.g., the columns of the array 905 include additional sensors 910), the number of pixels along the length of the pressure image 1000 may also increase. By viewing the colors (or shades of a color) in the pressure image 1000, a user can determine the pressure values exerted by the arm on the band 900. Moreover, by generating the image 1000, the pressure imager can used video processing techniques to evaluate the image and identify gestures.

Figure 11:
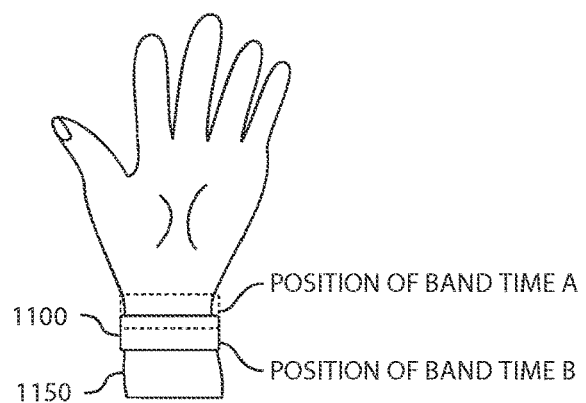
FIG. 11 illustrates an arm band located at different positions on an arm, according to one embodiment described herein.

FIG. 11 illustrates an arm band 1100 located at different positions on an arm 1150, according to one embodiment described herein. Specifically, FIG. 11 illustrates the band 1100 at two different locations of the arm at two different times—i.e., Time A and Time B. In one embodiment, the different positions at Time A and Time B may result from the user taking off the band and then putting the band back one. Or the different positions may result from the user adjusting the band (without taking it off) after the original position at Time A became uncomfortable.

In one embodiment, the band 1100 and pressure imager are calibrated to detect hand gestures. For example, during the calibration process, the pressure imager may ask the user to perform different gestures while the band 1100 is located in the position shown at Time A. As the user makes the different gestures, the pressure imager captures respective pressure images. Because of the 2D array of pressure sensors, the pressure images may provide a more robust technique for distinguishing between hand gestures relative to measuring a change in thickness as discussed above. After the calibration process is complete and the user makes a gesture, the pressure imager can compare the current pressure image to the images captured during calibration. Using video processing techniques, the pressure imager can determine a similarity between these images to determine a match (e.g., according to predefined threshold). In one embodiment, the pressure imager may do a pixel-to-pixel comparison to determine a similarity score between the images. In another example, the imager may average color values for a group of pixels and compare them to other pixels that correspond to the same location in the sensor array on the band. Regardless of the specific technique used to compare the images, the pressure imager can identify hand gestures by correlating pressure images taken of the user's arm with images captured during calibration.

However, if the user moves the band on the arm, then the images taken during calibration and the images taken after the band was moved do not correlate to the same portion of the user's arm. For example, the user may remove the arm band 1100 at Time A and then, when placing the arm band 1100 back on the wrist at a Time B, move the band 1100 to a different location. For example, even if the user twists the band around the wrist but otherwise keeps the band at the same lateral location on the wrist, the pressure images taken at Time A (e.g., during calibration) are offset from the ones captured after the band is moved at Time B. Using the pressure image 1000 shown in FIG. 10 as an example, if the user rotates the band, the first and second portions 1005, 1010 shift in the image 1000. If the user rotates the band clockwise, the first and second portions 1005, 1010 may shift to the right. If the band is rotated counterclockwise, the portions 1005, 1010 shift to the right. If the user moves the band lateral on the arm towards the hand, the lower portion of the image 1000 may be cut off and replaced by color values corresponding to tendon movement at a portion of the arm closer to the hand. Conversely, if the band is slid down the arm closer to the elbow, an upper portion of the image 1000 would not be absent from the image 1000 and replaced by color values corresponding to tendon movement at a portion of the arm closer to the elbow.

If the pressure imager compares the images taken after the band is moved to images captured during calibration, detecting hand gestures becomes more difficult and may be impossible. Again using FIG. 10 as an example, if this image 1000 was taken during the calibration process when the user was making Gesture A but then the user rotates the band and makes the same gestures, the first and second portions 1005, 1010 will be located at different portions in the image 1000. For example, instead of displaying color/gray-scale values indicating low pressure values, the first portion 1005 of image 1000 may contain colors indicating high pressure values. Thus, the pressure imager may erroneously determine that the user is not making the same gesture used to calibrate the band even though she is.

Figure 12A:
FIGS. 12A and 12B illustrate correlating pressure images captured at different locations on the arm, according to one embodiment described herein.
Figure 12B:
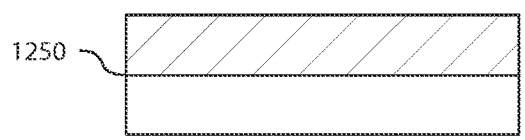

If the band was moved latterly on the user's arm as shown in FIG. 11, only certain portions of the pixels may match. FIGS. 12A and 12B illustrate correlating pressure images captured at different locations on the arm, according to one embodiment described herein. In this example, pressure image 1200 may be captured at Time A in FIG. 11 while pressure image 1250 is captured at Time B when the band is moved laterally down towards the user's elbow. Assume in this embodiment that the band was not rotated when it was moved.

Even though the band was moved, different locations of the 2D sensor and the captured images 1200, 1250 overlap. That is, a region of image 1200 includes pressure information about the same location of the arm as a region of image 1250. The overlap (or common) regions of images 1200 and 1250 are illustrated by the hatched portions of these images. In this example, the lower region of image 1200 corresponds to the upper region of image 1250. If the user was making the same gesture, the pressure information in the lower region of image 1200 should match the pressure information in the lower region of image 1250. Put differently, the color/gray-scale values of the pixels in these overlapping regions should match if the same gesture is made.

In one embodiment, the pressure imager does not need to compare all of the pixels in two pressure images to determine that the user is making the same gesture. Put differently, the pressure imager may be able to distinguish between different gestures only by evaluating a portion of the pressure images. Because the pressure information contained in the non-hatched regions of image 1200 does not correspond to any portion of image 1250, the pressure imager may ignore this region of image 1200 and compare only the hatched regions of images 1200, 1250. Thus, even if the user moves the band, so long as the pressure images still overlap, the pressure imager can compare the overlapping portions and determine if the user is making the same hand gestures that were made during the calibration process.

Figure 13:
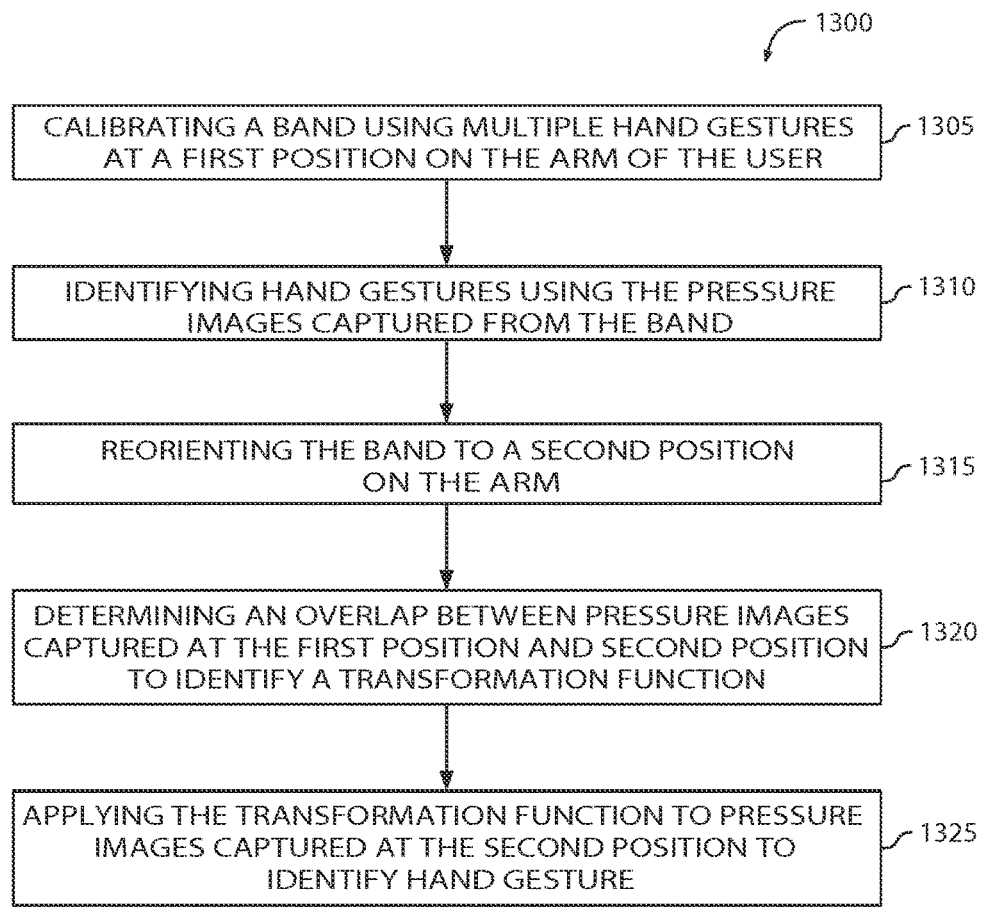
FIG. 13 is a flow chart illustrating a method for detecting hand gestures using an arm band, according to one embodiment described herein.

FIG. 13 is a flow chart illustrating a method 1300 for detecting hand gestures using an arm band, according to one embodiment described herein. At block 1305, the pressure imager calibrates the arm band (e.g., arm band 900 in FIG. 9) using multiple hand gestures when the arm band is at a first arrangement on the arm of the user. To do so, the pressure imager may use an I/O device such as a display screen or speaker to output instructions to the user. For instance, the pressure imager may ask the user to make Gesture A. The band may include another I/O device (e.g., a button) which the user presses once she has made the requested hand gesture. After the user makes the gesture, the imager uses a 2D sensor array contacting the arm of the user to generate a pressure image as described above. This process may repeat for a predetermined number of gestures.

Furthermore, the calibration process may allow the user to make her own gestures. For example, if the user would like to program the pressure imager to identify a special gesture, she may make the gesture while the pressure imager captures the corresponding pressure image. As such, the pressure image can be customized to identify both predetermined and user-generated gestures.

At block 1310, the pressure imager identifies hand gestures using the pressure images captured from the band. In one embodiment, the pressure imagers use video processing techniques to determine similarity scores between the current captured image and the images captured during the calibration process at block 1305. Whichever comparison yields the highest similarity score may be selected by the imager as the matching image. The pressure imager determines that the gesture corresponding to the matching image is the gesture currently being made by the user. As mentioned above, the similarity score may be derived by performing a pixel-by-pixel analysis between the images, comparing average color values for groups of pixels in the images, and the like.

In one embodiment, the pressure imager may use a predetermined threshold to prevent false positives. For example, when comparing the currently captured pressure image to the images captured during calibration the pressure imager does not determine a similarity score that exceeds the threshold, the imager may indicate to the user or an application that it was unable to determine a match. The pressure imager may ask the user to tell it what gesture is currently being made, or the imager may repeat the calibration process.

At block 1315, the user reorients the band to a second arrangement on the arm of the user after the calibration process was performed. For example, the user may rotate the band or move the band latterly to a more comfortable position on the arm. Or the user may remove the band and then slid the band back onto the arm. In any case, the images now captured by the band no longer contain pressure information about the same exact region of the arm as the images captured during calibration. That is, at least some pixels in the pressure images generated after the arm band is moved represent pressure data for a portion of the arm that is not contained in the images captured at calibration.

At block 1320, the pressure image determines an overlap between pressure images captured at the first arrangement and the second arrangement to identify a transformation function. That is, even if the band is rotated or moved latterly, the images at the different positions still contain pressure information corresponding to a common region of the user's arm. This overlap region is one advantage of using a band that includes a 2D array of sensors. If just a ring of sensors was used—i.e., a single row of sensors around the circumference of the arm band—if the user moves the band latterly, the pressure images generated using the ring of sensors do not have any overlapping portions with the images captured at the new location of the band. However, by using a 2D array of sensors that extends latterly along the arm, the system increases the likelihood that even if the user slides the band latterly along the arm, the images captured at the two different locations will contain pressure information for an overlapping portion of the user's arm as shown in FIGS. 11 and 12A-12B. Even though a ring of sensors (e.g., a 1D sensor) may be sufficient for distinguishing between gestures once the calibration process is performed, this type of sensor is intolerant to lateral movements of the band along the arm, unlike the 2D sensor array.

In one embodiment, block 1320 is performed after the user indicates that the arm band has been reoriented. For example, after removing the band, the user (or an application) may inform the pressure imager that the user has put the arm band back on. In another example, the user may put on the arm band after an application (e.g., a video game) begins to execute. By signing into a user account, the pressure imager can determine that the calibration process has been performed previously, and thus, does not need to be repeated. Alternatively, the pressure sensor may determine to perform block 1320 if too many mismatches have occurred—i.e., the pressure imager has been unable to match the current pressure image to an image captured during calibration a predetermined number of times. In response, the pressure imager may assume that the user has reoriented the band.

In one embodiment, the pressure imager may ask the user to perform a single gesture in order to determine the overlap between the different positions and generate the transformation gesture. That is, instead of instructing the user to make all the different gestures used to calibrate the band, the imager asks the user to perform one or two gestures. Once the image is captured at the new location, the pressure imager compares the new image to the old image captured when making the same gesture during calibration to determine the overlap. In one embodiment, the pressure imager may use the same comparison techniques discussed at block 1310 to identify regions in the images that contain similar color/gray-scale values. The pressure imager may perform a search of one image to determine if a particular portion of the new image matches a portion in the old image. Referring to FIGS. 12A and 12B, the pressure imager may determine that the lower region in the old image 1200 contains color values that match the color values in the upper region of the new image 1250.

In addition to performing a lateral search to identify commonality between the old and new images, the pressure imager may rotate the images to see if doing so causes regions in the old and new images to align. For example, in addition to moving the arm band to a different lateral position, the user may have rotated the band relative to its orientation at the old position, and as such, the pressure imager may need to rotate the images before the similarity between the upper and lower regions of the new and older regions is identified.

Once the overlapping region in the old and new images is identified, the pressure imager generates a transformation function for comparing the images captured at the new location of the band to the images captured at the old location when the calibration process was performed. For example, if the band was moved latterly, the transformation function may include comparing only a sub-portion of the captured images to a corresponding sub-portion of the images captured during calibration. The transformation function may include a list of pixel rows in the captured images which should be ignored and which should be used to match with the images captured during calibration. Moreover, if the band was rotated, the transformation function may include a shift that should be performed on the captured images before they are compared to the images captured when the arm band was calibrated. This shift effectively cancels out the clockwise or counter-clockwise rotation of the band on the arm. Of course, the transformation function may compensate for both a lateral movement of the band as well as a rotational movement of the band. For example, the transformation function may include using one sub-portion of the captured image (and ignoring the remaining portion of the image) as well as shifting the sub-portion of the image.

At block 1325, the pressure imager uses the transformation function to adjust the captured images so they can be compared to the images generated during calibration at block 1305. As discussed, the pressure imager may compare the upper rows of pixels in the captured image to the lower rows of pixels in the images generated during calibration and/or shift the captured image to compensate for a rotational change in the band. Moreover, the pressure imager may perform a transformation function on the images captured during calibration. That is, certain rows of these images may be ignored (if the band was moved laterally).

Once the transformation function is performed, the pressure imager compares the overlapping regions in the captured image and the images taken during calibration to identify the gesture currently being made by the user. That is, the pressure imager does not need to evaluate all of the images in order to determine the similarity score described at block 1310. Indeed, the pressure imager may need to identify and compare only one row of pixels in the currently captured images with one row of pixels in the images generated during calibration to determine if the current hand gesture matches one of the calibration gestures. However, adding additional rows of pixels may improve the accuracy of the pressure imager.

Figure 14:
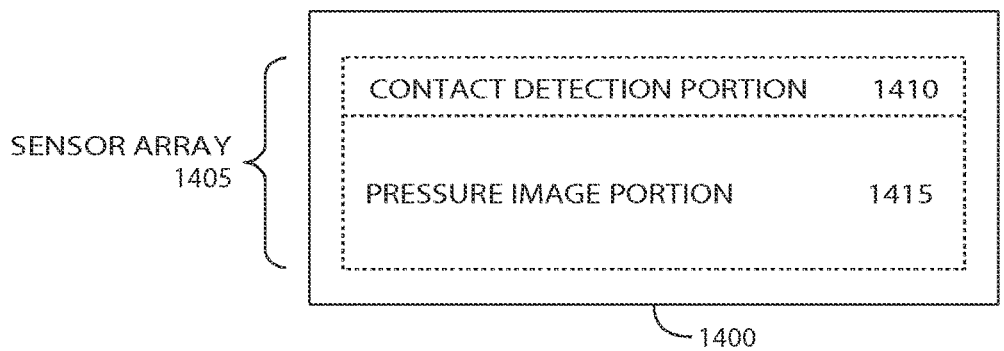
FIG. 14 illustrates an arm band where different portions of the 2D sensor array perform different functions, according to one embodiment described herein.

FIG. 14 illustrates an arm band 1400 where different portions of a 2D sensor array 1405 perform different functions, according to one embodiment described herein. In arm band 1400, the sensor array 1405 is divided into a contact detection portion 1410 and a pressure image portion 1415. The contact detection portion 1410 may include one or more rows of pressure sensors that enable the pressure imager to determine if this portion 1410 of the band 1400 is contacting the arm of the user. In contrast, the pressure image portion 1415 may include one or more rows of pressure sensors that output the sensor data used to generate the pressure images described above.

In one embodiment, the pressure sensors in the contact detection portion 1410 may not be mounted on a flexible or pliable material (e.g., the inner portion 902 shown in FIG. 9) but instead directly mounted on a rigid material (e.g., the output portion 901). By mounting the sensors on a rigid material, the pressure values generated by these sensors may better indicate whether the portion 1410 is contacting the user's arm. By determining if the user's arm contacts the portion 1410, the imager can estimate the size of the user's arm and adjust how it evaluates the pressure images generated using the sensors in the pressure image region 1415.

A person with an arm with a smaller diameter may mean that the user's arm does not contact the sensors located in the contact detection portion 1410. Based on this information, the pressure imager can scale the image generated using the sensors in the pressure image portion 1415. For example, if the image pressure determines the user's arm is not contacting portion 1410 of the array 1405, it can ignore these pressure values when generating the pressure image. Instead, the pressure imager may focus on the pressure values identified in portion 1415 to provide a more detailed view of the tendon movement in the corresponding region in the user's arm.

Figure 15:
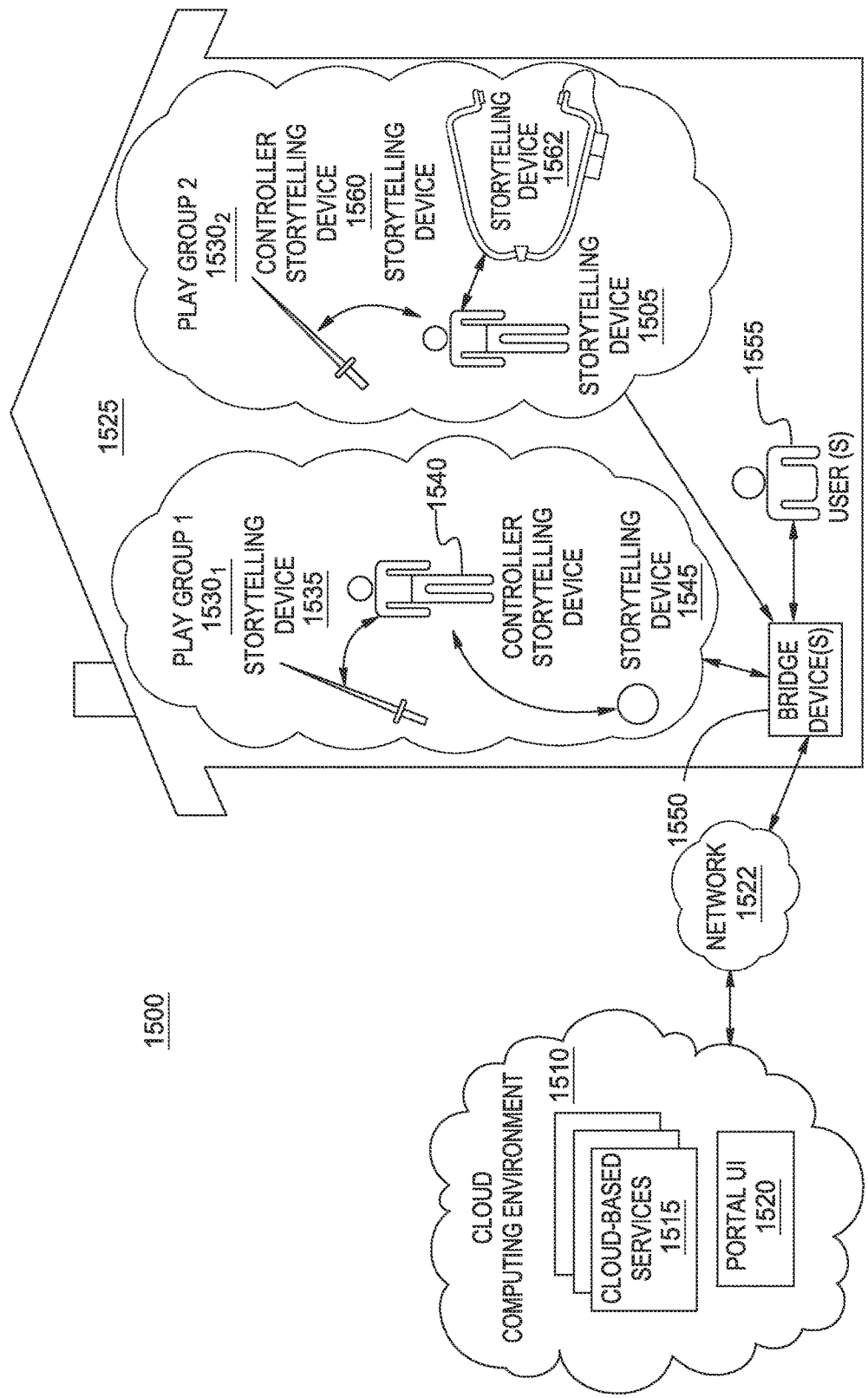
FIG. 15 illustrates an example storytelling environment that includes an arm band, according to one embodiment described herein.

FIG. 15 illustrates an example storytelling environment, according to one embodiment. As shown, the environment 1500 includes a cloud computing environment 1510 and a home environment 1525, interconnected via network 1522. The home environment 1525 includes two playgroups 1530$_{1-2}$ of storytelling devices, as well as a user(s) 1555 and a bridge device(s) 1550. Here, the user may connect to the bridge device 1550 via an application (e.g., executing on a mobile device, rendered within a web browser, etc.). The cloud computing environment 1510 hosts a plurality of services 1515 and a portal user interface 1520.

Generally, cloud computing generally refers to the provision of scalable computing resources as a service over a network. More formally, cloud computing may be defined as a computing capability that provides an abstraction between the computing resource and its underlying technical architecture (e.g., servers, storage, networks), enabling convenient, on-demand network access to a shared pool of configurable computing resources that can be rapidly provisioned and released with minimal management effort or service provider interaction. Thus, cloud computing allows a user to access virtual computing resources (e.g., storage, data, applications, and even complete virtualized computing systems) in "the cloud," without regard for the underlying physical systems (or locations of those systems) used to provide the computing resources.

Typically, cloud computing resources are provided to a user on a pay-per-use basis, where users are charged only for the computing resources actually used (e.g. an amount of storage space consumed by a user or a number of virtualized systems instantiated by the user). A user can access any of the resources that reside in the cloud at any time, and from anywhere across the Internet. Doing so allows a user to access information and the services 1515 from any computing system attached to a network connected to the cloud (e.g., the Internet).

Each playgroup $1530_{1-N}$ generally represents a set of storytelling devices involved in a unique storytelling or playtime experience. For instance, the playgroup $1530_1$ represents a science fiction-themed storytelling experience and includes a light sword storytelling device 1535, an action figure controller storytelling device 1540, and a trainer storytelling device 1545. Likewise, the playgroup $1530_2$ also represents a science fiction-themed storytelling experience and includes a light sword controller storytelling device 1560, an armband storytelling device 1562 (e.g., arm band 105 in FIG. 1), and an action figure storytelling device 1565. More generally, however, the playgroups may contain any number of storytelling devices of any number of different themes and types.

Generally, the playgroups 1530 include storytelling devices within a particular physical location (e.g., a room of the house environment 1525). That is, in one embodiment, it may be preferable for a storytelling experience to only interact with storytelling devices within its immediate physical proximity (e.g., within the same room), as to do otherwise can potentially create security and other problems during the storytelling experience. A number of different techniques may be used to determine which storytelling devices are within immediate physical proximity of one another. For example, the arm band storytelling device 1562 could emit a first signal (e.g., an infrared signal) and the other storytelling devices could be configured to transmit a response (e.g., a radio frequency signal (RF)) upon receiving the first signal. The storytelling device(s) could then receive the responses from the other storytelling devices and could create a playgroup 1530 that includes the other storytelling devices as well as the arm band storytelling device 1562.

As shown, the devices 1540 and 1560 have been elected as controller devices within the playgroups $1530_{1-2}$. Generally, a controller device configures each of the storytelling devices within a playgroup to perform certain actions in response to a detected stimulus event and a current context of the story being told. Here, the story may include a number of different contexts in a temporal order, and the playback of the story may advance from one context to the next until the last context is reached and the storytelling experience is complete. However, while the story may be linear in progression, this is not necessary. For example, a story could have different branches, where the story can proceed down one of many possible arcs. For instance, arcs could be randomly selected, selected based on a user's request (e.g., the user specifying which arc should be taken), selected based on the user's actions (e.g., the user manages to "rescue" one of the fictional characters in the story), selected based on the user's history of actions (e.g., whether the user is trending towards the "dark side" in a science fiction storyline), and so on. Moreover, the story may be modified dynamically during playback based on various actions, such as one of the storytelling devices becoming unavailable (e.g., losing power, leaving the physical environment, etc.) or a new storytelling device being introduced to the environment (e.g., the user's friend comes over to play, bringing one or more new storytelling devices with him).

Additionally, the controller may maintain state information and control game logic for the playgroup 1530. For example, playgroup $1530_2$ could be playing out a story in which a user is asked by the action figure device 1565 to handle a virtual object using gestures detected by the arm band device 1562. Here, the elected controller device (i.e., action FIG. 1560) could maintain "training" points for the user that is decremented when the user fails to handle the virtual object properly, and could further maintain a count of the different gestures the user has learned thus far. Additionally, the controller could retrieve state data for the user (e.g., by querying one of the cloud-based services 1515 with an identifier for the user) and could use the user state data to adjust the playback of the story.

In addition to detecting nearby storytelling device within the same physical environment, the storytelling devices within a playgroup 1530 may elect one of the storytelling devices as a controller storytelling device. A number of different techniques may be used for such an election. For example, a user could explicitly specify that a particular one of the storytelling devices (e.g., the user's favorite device) should be used as the controller. Here, it may be preferable for the user to select a device that will remain with the user throughout the storytelling experience, so as to avoid a subsequent controller election part-way through the story. In one embodiment, the controller may be elected based on technical specifications and properties of the storytelling devices. For example, a storytelling device with a substantial amount of memory, processing power and communication bandwidth may be preferable as the controller, relative to a device having a lesser amount of computing resources.

As discussed above, the story may generally include stimulus events and corresponding actions, and may be linear in progression or dynamic (e.g., a story that includes different story arcs or branches). In one embodiment, the story may be defined such that each corresponding action is attribute to a type or role of storytelling device (i.e., as opposed to a specific storytelling device). In mapping the story to the available and compatible storytelling devices, the controller device 1520 could determine a type of each of the storytelling devices, and could assign particular stimulus events and corresponding actions to each of the storytelling devices based on the determined type. For example, a particular story could state that an action should be performed by a storytelling device having the role of "Hero", and the controller could map the action onto a storytelling device within the playgroup having the role "Hero".

Once the controller maps the story onto the devices, the controller configures each of the storytelling devices with a number of stimulus events and corresponding effects relating to a first context of the story. As an example, the action FIG. 1540 could detect when the user has successfully deflected a virtual laser fired from the storytelling device 1545 (i.e., an occurrence of the stimulus event), and could audibly congratulate the user in response (i.e., performing the corresponding effect).

In the preceding, reference is made to embodiments of the invention. However, it should be understood that the invention is not limited to specific described embodiments. Instead, any combination of the above features and elements, whether related to different embodiments or not, is contemplated to implement and practice the invention. Furthermore, although embodiments of the invention may achieve advantages over other possible solutions and/or over the prior art, whether or not a particular advantage is achieved by a given embodiment is not limiting of the invention. Thus, the aspects, features, embodiments and advantages are merely illustrative and are not considered elements or limitations of the appended claims except where explicitly recited in a claim(s). Likewise, reference to "the invention" shall not be construed as a generalization of any inventive subject matter disclosed herein and shall not be considered to be an element or limitation of the appended claims except where explicitly recited in a claim(s).

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order or out of order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

While the foregoing is directed to embodiments of the present invention, other and further embodiments of the invention may be devised without departing from the basic scope thereof, and the scope thereof is determined by the claims that follow.

What is claimed is:

1. An arm band, comprising:
a first portion;
a second portion;
a pivoting element coupled to respective first ends of the first and second portions, wherein the pivoting element permits respective second ends of the first and second portions opposite of the first ends to separate relative to each other; and
a sensor configured to, when the arm band is worn on the arm, generate an output signal indicative of a thickness of the arm in a direction substantially perpendicular to a palm of a hand.

2. The arm band of claim 1, wherein the sensor comprises a first sensing portion at the second end of the first portion and a second sensing portion at the second end of the second portion, wherein as the first and second portions pivot, the sensor is configured to change the output signal as a distance between the first and second sensing portions changes.

3. The arm band of claim 2, wherein the sensor is a magnetometer and one of the first and second portions is a permanent magnet.

4. The arm band of claim 1, where the first and second portions each comprise a respective flat surface between the first and second ends, wherein the flat surfaces are configured to be perpendicular to the palm of the hand when contacting the arm.

5. The arm band of claim 1, further comprising:
a clamping element configured to force the second ends of the first and second portions to pivot closer together.

6. The arm band of claim 5, wherein the clamping element comprises a spring at least one of integrated into the pivoting element and located at the first end of one of the first and second portions.

7. The arm band of claim 1, further comprising:
a latching mechanism disposed on the second ends of the first and second portions, the latching mechanism comprising a receiving element, an elastic band, and a connector ball, wherein the connector ball is attached to the elastic band, and wherein the receiving element defines an aperture for receiving the connector band, thereby latching the first portion to the second portion.

8. The arm band of claim 1, wherein the sensor is configured to measure at least one of a current, a voltage, and a resistance associated with a current path in the arm band, wherein the current path includes the first and second portions and the pivoting element, and wherein the at least one current, voltage, and resistance measured by the sensor changes as the thickness of the arm changes.

9. A system, comprising:
an arm band comprising:
a first portion,
a second portion,
a pivoting element coupled to respective first ends of the first and second portions, wherein the pivoting element permits respective second ends of the first and second portions opposite of the first ends to separate relative to each other, and
a sensor configured to, when the arm band is worn on the arm, generate an output signal indicative of a thickness of the arm in a direction substantially perpendicular to a palm of a hand, and
a computing device configured to receive the output signal and determine a hand gesture causing the thickness of the arm to change.

10. The system of claim 9, wherein the computing device is configured to compare the output signal to one or more threshold to distinguish between a plurality of predefined hand gestures.

11. The system of claim 9, wherein the computing device is configured to determine the hand gesture based on a rate of change in the output signal.

12. The system of claim 9, wherein the sensor comprises a first sensing portion at the second end of the first portion and a second sensing portion at the second end of the second portion, wherein as the first and second portions pivot, the sensor is configured to change the output signal as a distance between the first and second sensing portions changes.

13. The system of claim 12, wherein the sensor is a magnetometer and one of the first and second portions is a permanent magnet.

14. The system of claim 9, wherein the arm band further comprises:
a clamping element configured to force the second ends of the first and second portions to pivot closer together.

* * * * *

UNITED STATES PATENT AND TRADEMARK OFFICE
CERTIFICATE OF CORRECTION

PATENT NO. : 10,067,564 B2  
APPLICATION NO. : 14/823685  
DATED : September 4, 2018  
INVENTOR(S) : Lanny S. Smoot et al.

It is certified that error appears in the above-identified patent and that said Letters Patent is hereby corrected as shown below:

In the Drawings

On sheet 5 of 8, in Figure 9, Line 6, delete "LENGH" and insert -- LENGTH --, therefor.

In the Specification

In Column 7, Line 10, delete "first," and insert -- fist, --, therefor.

In Column 7, Line 14, delete "first" and insert -- fist --, therefor.

In Column 8, Line 44, delete "first," and insert -- fist, --, therefor.

In Column 8, Line 48, delete "first" and insert -- fist --, therefor.

In Column 14, Line 34, delete "at a" and insert -- at --, therefor.

In Column 20, Line 11, delete "FIG. 1560)" and insert -- action figure 1560) --, therefor.

In Column 20, Line 56, delete "FIG. 1540" and insert -- action figure 1540 --, therefor.

Signed and Sealed this  
Eleventh Day of December, 2018

Andrei Iancu  
*Director of the United States Patent and Trademark Office*